United States Patent [19]

Okarma et al.

[11] Patent Number: 5,022,988
[45] Date of Patent: Jun. 11, 1991

[54] DEVICE FOR PLASMA MODIFICATION—COMPOSITION AND REMODELING

[75] Inventors: Thomas B. Okarma, Palo Alto; Chin-Hai Chang, Los Altos; Brian R. Clark, Redwood City; L. Bernard Lerch, Menlo Park, all of Calif.

[73] Assignee: Applied ImmuneSciences, Menlo Park, Calif.

[21] Appl. No.: 260,382

[22] Filed: Oct. 20, 1988

Related U.S. Application Data

[63] Continuation-in-part of Ser. No. 191,039, May 19, 1988, Pat. No. 4,963,265.

[51] Int. Cl.⁵ .............................. B01D 63/08
[52] U.S. Cl. ..................... 210/321.84; 210/321.86; 210/502.1; 210/908; 435/287; 436/178; 502/404; 530/412; 530/814
[58] Field of Search .............. 210/634, 635, 638, 645, 210/646, 651, 660, 691, 371.72–371.90, 502.1, 908; 604/4–6; 435/269, 287, 299, 803, 815; 436/178, 824; 530/380, 412, 812, 814; 424/101; 502/407, 410, 401, 404

[56] References Cited

U.S. PATENT DOCUMENTS

| | | | |
|---|---|---|---|
| Re. 31,688 | 9/1984 | Popovich et al. | 210/651 |
| 4,086,924 | 5/1978 | Latham, Jr. | 604/6 |
| 4,103,685 | 8/1978 | Lupien et al. | 604/6 |
| 4,223,672 | 9/1980 | Terman et al. | 604/5 |
| 4,362,155 | 12/1982 | Skurkovich | 604/6 |
| 4,428,744 | 1/1984 | Edelson | 604/6 |
| 4,464,165 | 8/1984 | Pollard, Jr. | 210/635 |
| 4,540,401 | 9/1985 | Marten | 604/28 |
| 4,614,513 | 9/1986 | Bensinger | 210/651 |
| 4,627,915 | 12/1986 | Kuroda et al. | 210/195.2 |
| 4,693,985 | 9/1987 | Degen et al. | 210/635 |

FOREIGN PATENT DOCUMENTS 0082345 11/1982 European Pat. Off.

OTHER PUBLICATIONS

McLeod, et al., *Artif. Organs* (1983) 7:443–449.
Breillatt and Dorson, *ASAIO J.* (1984) 7:57–63.

*Primary Examiner*—W. Gary Jones
*Attorney, Agent, or Firm*—Irell & Manella

[57] ABSTRACT

Compositions and devices are provided for the specific removal of components of plasma in efficient and economical ways. The devices provide for a tortuous path of the plasma through a high surface material to which is bound a binding compound for removal of the fluid component. The devices find particular application with plasma, in diagnosis, therapy, and for production of specific physiologically active materials.

8 Claims, 3 Drawing Sheets

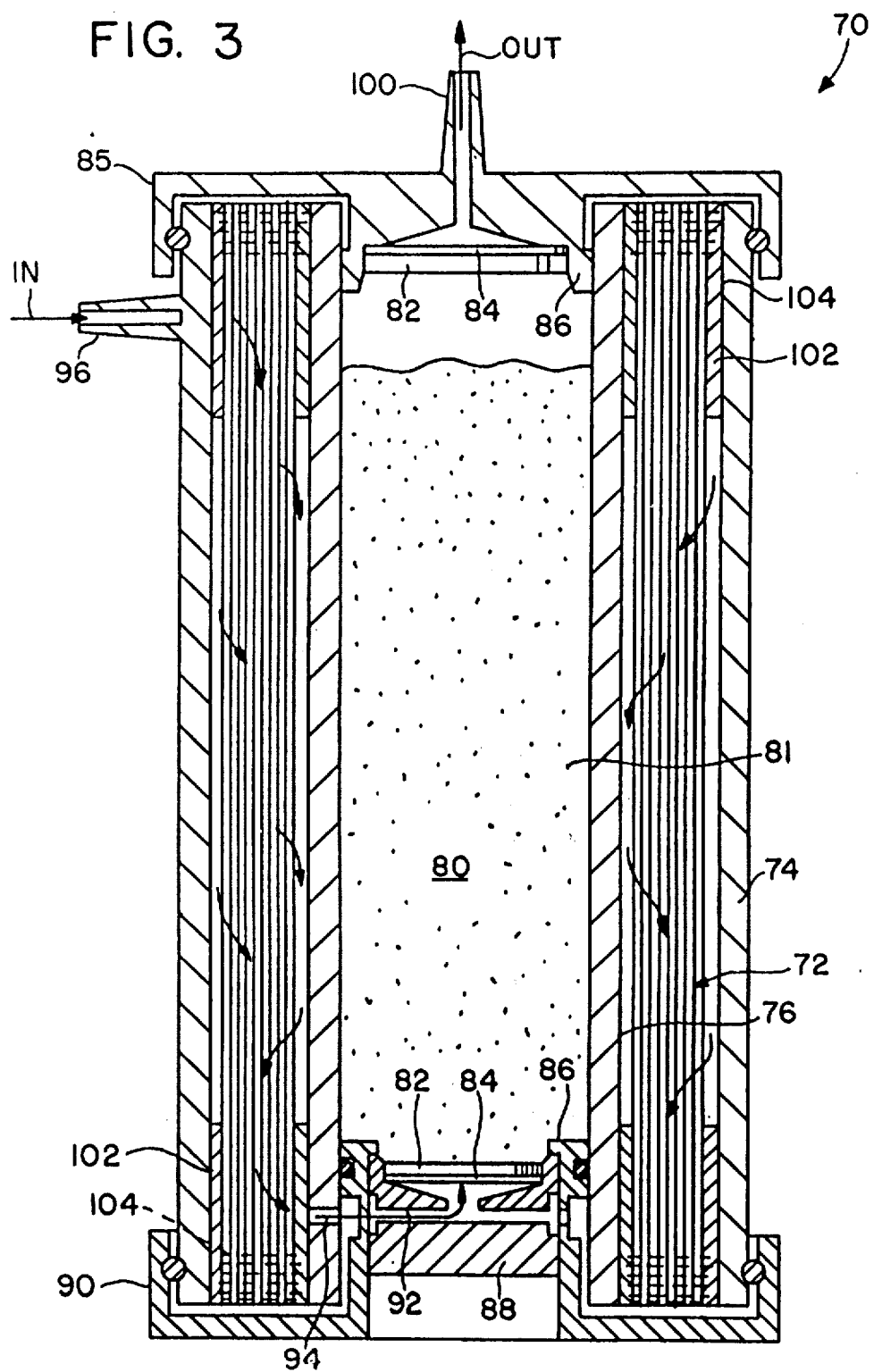

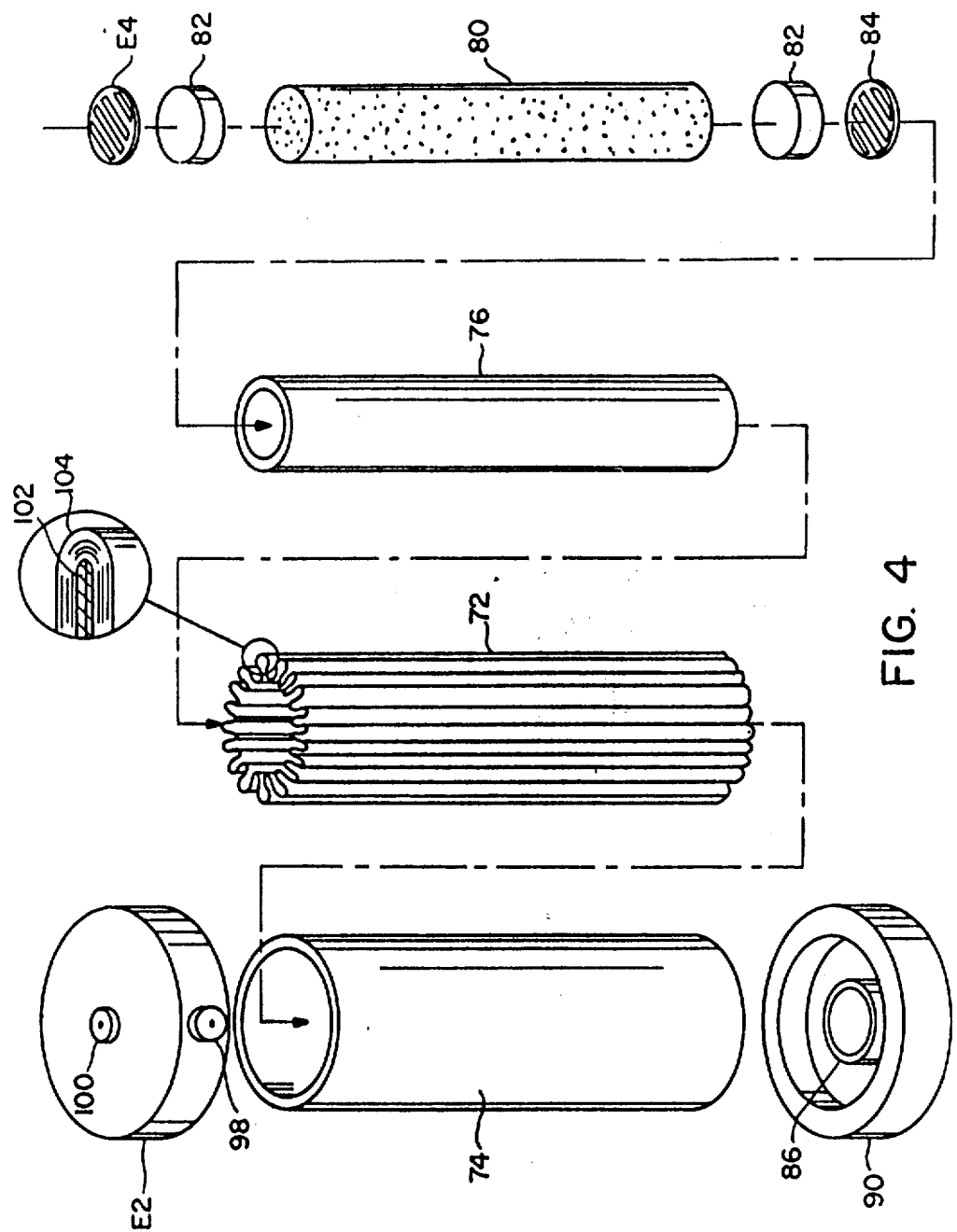

DEVICE FOR PLASMA MODIFICATION—COMPOSITION AND REMODELING

CROSS-REFERENCE TO RELATED APPLICATION

This application is a continuation-in-part of application Ser. No. 191,039 filed May 6, 1988, now U.S. Pat. No. 4,963,265.

INTRODUCTION

1. Technical Field

The subject invention is concerned with plasma processing devices involving separation of soluble plasma components and remodeling of soluble plasma components.

2. Background

Blood and lymph are the fluid highways of the body. These fluids provide for the transport of nutrients, metabolites, growth factors, hormones, and the like, from one site in the body to another, allowing for production of various compounds by cells and tissues in one part of the body, for the regulation of cells and tissues in another part of the body. In addition, these fluids allow for removal of waste materials, so as to prevent the accumulation of compounds which could interfere with the ability of cells and organs to function. Of equal importance is the fact that these fluids also allow for transport of cells of the hematopoietic system throughout the body to fulfill their variegated function, while also bringing a wide variety of materials to cells of the hematopoietic system for processing or for inducing a cellular response, as in the case of antigens, pathogens, or the like.

In many situations, the interaction between substances in the blood and hematopoietic cells can result in products which may provide fruitful information about the diseased state of the individual, provide compositions of interest in relation to the host or other individuals, or cause adverse affects to the host. There is, therefore, a substantial interest in accessing these fluids and isolating, identifying or remodeling various components in the blood stream.

Blood, however, is an extraordinarily complex mixture, which may respond to an alien environment in a wide variety of ways. Commonly, blood clots result in the stoppage of flow. Where plasma is used, contact with foreign materials can activate various blood components resulting in substantial changes in the blood composition. While this may not be a problem in many instances where the blood or plasma is not being reused, when the blood is to be returned to the host, such changes many detrimentally affect the host and therefore preclude the reuse of the blood.

In many instances, it is desirable to restore a person's blood, such as in plasmapheresis, because of the uncertainties concerning the safety of the blood supply, due to hepatitis, HIV, HTLV-I, or the like, or the availability of the correct blood type.

It is therefore of interest to develop procedures and equipment which allow for selective treatment of blood or plasma, by modification of the nature and/or amount of components of the blood and saving the blood for restoration to the host from which the blood was withdrawn. Necessary for this purpose is identification of materials, components, and conditions which allow for such selective treatment without significant adverse effects on the blood.

3. Relevant Literature

Descriptions of blood component removal systems may be found in U.S. Pat. Nos. 4,086,924; 4,103,685; 4,223,672; 4,362,155; 4,428,744; 4,464,165; 4,540,401; 4,614,513; 4,627,915 and Re 31,688 and EPA 0 082 345. References associated with complement activation include Breillatt and Dorson, *ASAIO J.* (1984) 7:57-63 and McLeod et al., *Artif. Organs* (1983) 7:443-449.

SUMMARY OF THE INVENTION

Devices are provided for the modification of blood or plasma involving removal or remodeling of blood components. The devices provide for an extended fluid path through a biocompatible high surface area packing to which is bound one or more specific binding components for interacting with one or more components of blood. The device allows for the smooth continuous flow of the fluid stream with substantially uniform contact between the fluid stream and the substrate-bound binding components. The device also allows for recovery of components of the blood which bind to the substrate-bound binding components. Particularly, a number of components produced by molecular biology techniques have been shown to be useful in blood treatment.

BRIEF DESCRIPTION OF THE DRAWINGS

FIG. 3 is a cross-sectional elevation of a tubular device according to this invention; and FIG. 4 is a perspective view of the parts of the device of FIG. 3.

DESCRIPTION OF THE SPECIFIC EMBODIMENTS

Figure 1:
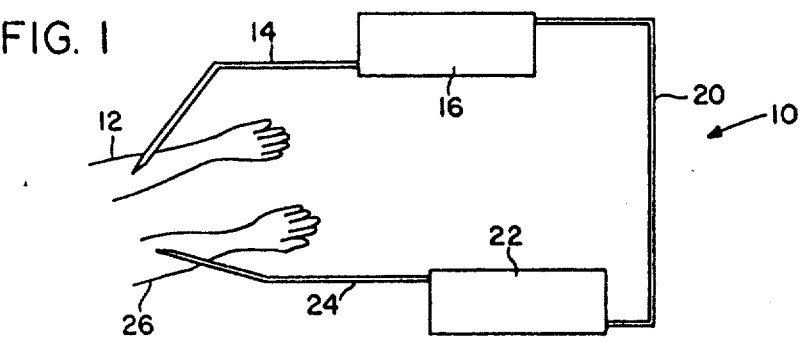
FIG. 1 is a diagrammatic view of a device according to this invention.

Methods and apparatus are provided for treating blood samples involving receptor-ligand complex formation on a solid surface which is biocompatible with blood or blood fluid derivatives. The fluid stream is directed through an extended, conveniently tortuous, path comprising a high surface area substrate to which a member of the specific binding pair is nondiffusibly bound. By interaction between components of the fluid stream and the bound specific binding component, one or more components of the blood stream will be removed or remodeled, by increasing or decreasing concentrations of such components or changing ratios of such components.

The blood stream may have been pretreated prior to use. The blood may have been subject to prior treatment, such as removal of red cells, platelets, white blood cells, or the like, where the resulting fluid may contain one or more families of cells or be substantially cell-free. Various compounds may be added such as acid-citrate, dextrin or heparin, and the blood stream may be diluted, concentrated, divided into two or more streams, or augmented with blood or blood component from the same or different host. The blood to be combined will be syngeneic or allogeneic.

The subject method may be used for a variety of purposes. In particular, members of a specific binding pair homologous to a component of interest may be employed to reduce the level of the component in the blood derived fluid. For example, immune complexes may be removed or remodeled by employing protein A, binding fragments thereof, or proteins having analogous binding properties, such as antibodies [other bacterial or mammalian Fc receptors] and the like. The antibodies may be specific for an epitope of a constant region isotype, e.g. IgM, IgG, IgA, IgD, or IgE or an epitope that crosses isotypes. Alternatively, antibodies present in the blood stream specific for a particular antigen may be removed by binding the antigen to the surface. Illustrative antigens include DNA or other host substances, particularly various factors involved with host responses to a diseased or aberrant state, such as tumor necrosis factor (TNF) associated with septic shock, or antibodies to the acetylcholine receptor in myasthenia gravis. In addition, there may be an interest in lowering a concentration of a particular component of the blood stream, such as insulin, neoplastic cells, steroids, e.g. estrogens, cytokines, lymphokines and other chemotherapeutic agents or biologicals employed as therapeutic agents. Thus, by varying the binding component present on the surface, the nature of the fluid stream may be modified in a single or multiple ways.

The fluid stream is directed, conveniently by pumping, through an extended path, conveniently a tortuous path, so as to expose the stream to a high level of binding component, while substantially minimizing adverse effects on the properties of the stream particularly those properties that cannot be reasonably rectified. As will be explained subsequently, the subject method is normally used in conjunction with further treatment since, under the conditions of complex formation, the level of anaphylatoxins normally increases.

The binding component will be nondiffusively bound, usually covalently bound, to a membrane surface, where the membrane will be composed of a plastic, e.g. cellulosic or polystyrene, biocompatible material. While other structures may find application, including structures such as porous beads, hollow fibers or the like, membranes may be used to advantage. In selecting a material, the selection will be based on biochemical compatibility, ease of functionalization, level of functionalization, degree of non-specific binding, with or without prior treatment, ease of fabrication, and the like.

Materials that may find application include nitrocellulose, cellulose, cellulose ester, e.g. acetate, nylon, polypropylene, polyethylene, silicone, polycarbonate, polyester, polyterephthalate, etc., or combinations thereof. The membranes will usually have pores in the range of about 1 to 500 $\mu$, more usually in the range of 2.5 to 25 $\mu$. A plurality of membrane layers will be employed. The layers may be in groups stacked one upon the other, where the stacks will have at least two membrane layers and may have ten or more membrane layers. The membrane stacks will be separated so as to allow for the relatively free flow of fluid through the membranes, while providing for a high surface area to ensure contact of the blood components with the bound component. Alternatively, a continuous spiral roll of membrane may be employed, where the flow is normal to a plane cutting through the spiral. Or, a fluted membrane may be used, where the fluted layers may be packed together about a central core or in parallel structures.

Depending upon the volumes to be treated, the surface area of porous surface will generally be in the range of about 0.2 to 3 m$^2$, more usually in the range of about 0.3 to 2.5 m$^2$. With a substantially cell free fluid, the rate of flow can be varied without concern as to cell lysis. Flow rates will generally be in the range of about 0.001 to 0.2 L/min, more usually in the range of about 0.002 to 0.1 L/min. Usually, the volume to be treated will be at least about 50 ml, more usually at least about 250 ml, and preferably at least about 500 ml.

The weight ratio of bound specific binding member to membrane support will vary widely depending upon the nature of the specific binding member. For the most part, protein binding members will be in the range of about 0.5 to 50, more usually about 1 to 20 mg/gram of membrane. The weight of binding member to volume of treated fluid may also be varied widely depending upon the specific binding member, but will generally be in the range of about 0.05 to 10, more usually about 0.1 to 5 mg/ml. Of course, depending upon the amount of the component which may be present in the fluid stream, larger or smaller amounts may be necessary to ensure that saturation is not achieved and that the capacity of the binding component bound to the membrane is sufficient for the amount of the fluid component which will be encountered.

One can provide for a tortuous path by having membrane pack or stack separators, which are effectively U-shaped and alternate in direction. Thus, the fluid flow would then be alternately redirected, so that the fluid will flow throughout the membrane pack in one direction, while flowing through the successive membrane pack in the opposite direction. The distance the fluid flows may vary widely depending upon the purpose of the treatment but will usually be a distance of at least about 10 cm to 220 cm, more usually about 20 cm to 40 cm.

The binding component will be bound to the support in a manner which minimizes leaching from the support during use and recovery of fluid components bound to the specific binding member. The manner of binding will, therefore, normally be covalent, where the surface of the membrane is functionalized. Various techniques for functionalization exist involving functionalized surfaces which may react with amines, carboxylic acids, activated aromatic rings, such as phenols as in tyrosines, active heterocycles, such as histidine, or the like. With saccharides, either as the membrane or the binding component, the saccharide may be cleaved to provide a dialdehyde which may then be condensed with an amine under reductive amination conditions. The resulting aliphatic amine linkage provides for a strong, noncleavable linkage, which allows for repeated reuse of the membrane, whereby blood components may be isolated and released from the membrane efficiently and in good yield. Where a polystyrene surface is employed, the surface may be functionalized using Freidel-Craft conditions for halomethylation, nitration, with subsequent reduction to amino groups, or the like, where the Freidel-Crafts reaction is carried out in tetramethylene sulfone or dimethylsulfoxide, particularly in the presence of under about 1% by volume of water. See, for example, copending application Ser. No. 051,917 filed May 19, 1987. The disclosure of this application is specifically incorporated herein by reference. Aromatic amino groups may be diazotized and used to form a diazo bridge to tyrosines or triazines. The triazines are a relatively unstable link and will usually not be employed.

Beside the membrane packs, other designs may be employed which provide for a large surface area for contacting the fluid stream. As already indicated, one could employ a membrane as concentric tubes or spirally wound around a core, where the flow would be parallel to the surface of the cylinder. One could provide for flow throughout the membrane in a single direction or have the flow be diverted in the opposite direction one or more times to greatly extend the path.

Instead of a membrane wound around a core, one could provide for a fluted membrane, where the folded membrane provides for exposure of the membrane surface to the fluid stream. Any technique to provide for complete exposure of the binding component on the surface, so that all the fluid is exposed to the opportunity for binding, while at the same time providing for efficient use of space and a low probability of clogging, may be employed. However, the use of the membrane sheet device has been found to be successful in providing a safe and efficient means for treating plasma and is, therefore, preferred.

It is found that when using the subject device, the formation of specific binding protein complexes results in a great enhancement in complement activation to anaphylatoxins. Since the anaphylatoxins can be detrimental if the plasma is restored to the host, the subject device will normally be employed with means for reducing a dangerous level of anaphylatoxins to a safe level. It is found that this can be achieved by passing the fluid from the subject device to a chamber containing silicic acid particles, where the silicic acid is found to substantially remove dangerous levels of anaphylatoxin, without a significantly deleterious effect on other components of the blood or the plasma characteristics. The anaphylatoxin removing device is described in copending U.S. application Ser. No. 191,039, filed May 6, 1988. The disclosure of this application is specifically incorporated herein by reference.

Briefly, the silicic acid particles will generally be of a size in the range of about 50 to 500 $\mu$, and of neutral and acidic pH in the range of about 3 to 7. The pore size will generally be in the range of about 50 to 350 Å with a surface area of at least about 200 m$^2$/g. The fluid stream, particularly plasma, from the subject device will generally be directed directly into the anaphylatoxin removing device.

The ratio of silicic acid to fluid generally will be in the range of about 10 to 100 g/L of fluid, more usually from about 15 to 50 g/L of fluid. The temperature will generally range from about 20° to 40° C., preferably from about 25° to 37° C. Ambient temperatures will usually be convenient.

To illustrate the subject invention, a cellulose acetate membrane may be employed. The membrane is a coating of cellulose acetate on an inert polyester support. The coating may vary in thickness, generally being at least about 100 $\mu$m to 200 $\mu$m, where the total thickness will range from about 150 to 500 $\mu$m, preferably about 150 to 300 $\mu$m. The cellulose acetate coating may be coated onto the support by any convenient means, using an appropriate volatile physiologically acceptable solvent. The cellulose acetate coating may then be activated in accordance with conventional techniques, for example, dilute periodate to provide for the desired level of activation. See, for example, U.S. Pat. Nos. 4,299,916 and 4,391,904.

The membrane may then be flushed with a dilute solution of a protein to be conjugated, e.g. protein A or acetylcholine receptor, where the solution may be perfused through the membrane pack for sufficient time to insure that the reaction has gone to completion and substantially all of the aldehyde groups have reacted. After mild flushing or perfusing with an appropriate buffer, conveniently a buffer more dilute than the buffer employed with the protein, so that non-covalently bound protein is removed, the membrane may then be reacted with a dilute borohydride solution to reduce the Schiff's bases or imines which were formed, so as to provide methyleneamines. Usually, a concentration of about 0.1 to 1M borohydride may be employed in appropriate dilute buffer, e.g. borate buffer. To insure the complete reaction, the reduction may be repeated one or more times, each time washing with dilute buffer after the reductive treatment.

Finally, the device may be treated with dilute saline of at least above 0.5M and not more than about 2M, followed by treatment with glycine of about 0.1 to 1M at an elevated temperature in the range of about 30° to 50° C. resulting in the complete removal of any residual borohydride and any protein which has not become covalently bonded. After flushing with PBS, the membrane is stabilized with dilute glycerol, generally at about 0.1 to 1% and may then be dried by any convenient means, e.g. centrifugation.

Any composition containing a lysine may be linked to the membrane in the manner described above. Thus, the above procedure provides for a simple and efficient technique for binding lysine containing compounds to a cellulosic surface in a manner which results in a low level of leaching, so that the bound protein does not contaminate any product which is extracted from the plasma and then eluted from the surface.

Instead of a cellulosic membrane, polystyrene or other biocompatible aromatic containing plastic may be used in the form of small particles which may be functionalized at the surface employing a nitrating medium in a tetramethylenesulfone solution in the presence of a small amount of water as described in copending application Ser. No. 051,917. The resulting nitrated polystyrene may then be reduced to amino groups, so as to have a plurality of aniline groups on the surface of the particles.

Antibodies, for example, may be oxidized in accordance with known techniques with periodate to provide for the dialdehydes as described previously for the cellulose acetate. Following the procedure described above for reductive amination between lysines of a protein and the activated cellulose surface, the activated antibodies may be combined with the particles to provide for reductive amination and antibody binding to the particles. In this manner, particles having antibodies bound to the surface in high concentration and functionalized so as to have the binding sites available can be produced.

After the plasma has circulated through the device and, as appropriate, been further treated to remove any anaphylatoxins, it may then be restored to the host in accordance with conventional techniques. Thus, the plasma may be removed and returned in a continuous manner or discontinuous manner, as appropriate.

The device containing the bound components may then be used in a variety of ways. The device may be restored by eluting the extracted component using an appropriate solution, such as a urea solution of about 2 to 10M, dilute acetic acid of about 0.1 to 0.8M, guanidinium salts of about 1 to 3M, or into 1 to 5M MgCl$_2$ or the like. The particular choice of eluent will vary depending upon the material of interest, wheththe material is to be recovered or discarded, the manner in which it may be subsequently used, or the like.

The subject device allows for collection of immune complexes, where the antigen may be identified and used in a variety of ways. The antigen may be used to identify a particular disease, to produce antibodies, used in other devices for monitoring the presence of antibodies, or for generating antigen-specific immune effector or regulatory cells. The antibodies may also be used for producing anti-idiotypes, to identify antigens in other samples, for sequencing, so as to produce probes to identify genes or mRNA in cells, or the like.

To further understand the subject invention, the drawings will now be considered. In FIG. 1, a schematic of the subject device is provided. The device 10 receives blood from one arm 12 of a patient through conduit 14. Conduit 14 introduces the blood into the first chamber 16, where one or more components may be exchanged, removed, or otherwise modified. The blood exits into conduit 20 and is directed by conduit 20 to anaphylatoxin removal chamber 22. The modified blood free of an undesirable level of anaphylatoxins is then directed through conduit 24 to the other arm 26 of the patient. In this manner, the blood has been modified in accordance with the needs of the patient and is returned to the patient free of elevated levels of anaphylatoxins to avoid potential shock.

Figure 2:
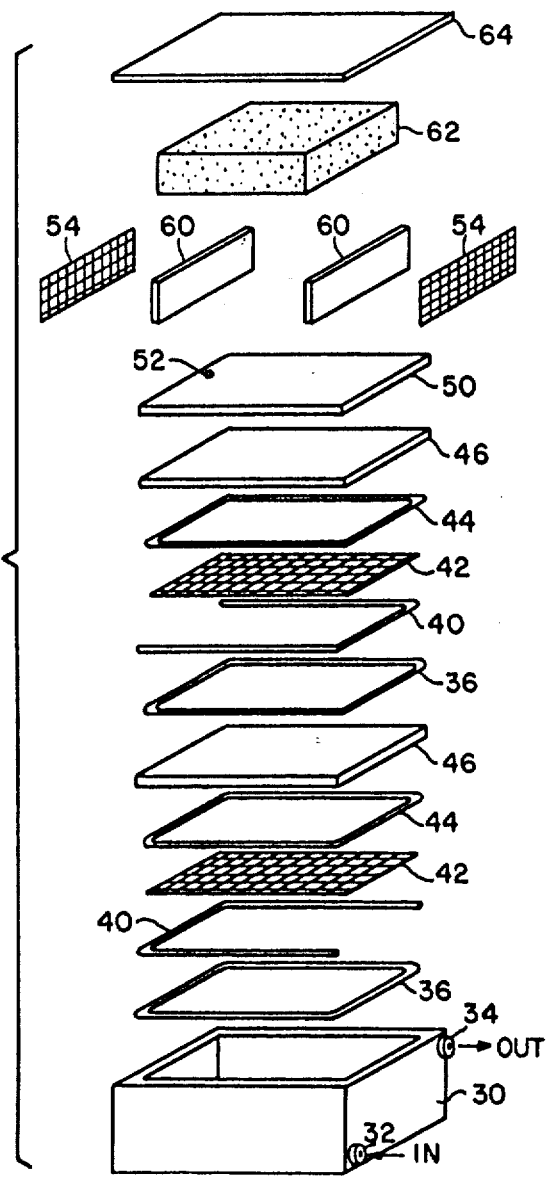
FIG. 2 is an exploded perspective view of a box device and its contents according to the invention.

In FIG. 2 is indicated an exploded view of a device in the shape of a box having first and second compartments where the first compartment has a plurality of membranes overlying one another and the second compartment has the silicic acid. The membrane compartment provides for an alternating direction of flow of the blood derived stream through the compartment. The device has a housing 30 with inlet 32 and outlet 34. Contained in the membrane compartment is O-ring 36, U-ring 40, and screen 42. The U-ring controls the direction of flow of the stream. On top of the screen 42 is a second O-ring 44 which separates the O-ring from membrane pack 46. The membrane employed may be Nalgene affinity chromatography unit bound with protein A, U12A or U38A (cat. nos. 751-2012 and 751-5038). The membrane pack will have a plurality of membranes lying one atop the other to which will be bound the specific binding pair members. Conveniently, each pack may contain from about 5 to 25, usually 5 to 20, membranes. The blood derived stream will pass up through the membrane pack 46 contacting the specific binding pair members and rising up through the pores to repetitively contact each succeeding membrane. Once the blood derived stream has passed through the membrane pack, the assemblage of O-ring 36, U-ring 40, positioned in the opposite direction of the previous U-ring 40, O-ring 36, screen 42, second O-ring 44 and membrane pack 46 may be repeated one or more times depending upon the size of the unit, the amount of material to be extracted, the binding capacity of the membrane packs and the like. The particular component which is the last component is not critical to this invention.

Various biocompatible materials may be employed for the various components. Conveniently, the O-ring and U-spacers may be high density polypropylene, the screens polypropylene and the housing polycarbonate.

Surmounting the components of the membrane compartment will be an inner lid 50 having port 52. The port 52 will be of approximately the same dimensions as the inlet and outlet ports 32 and 34 respectively of the housing 30. A polyethylene filter, not shown, conveniently of a pore size of 35-60 μ is applied across the port to prevent access of silicic acid particles into the membrane pack compartment. Barriers 54 and 60 are employed to maintain the silicic acid within a predetermined area in the silicic acid compartment. The silicic acid particles are indicated as a box 62. The silicic acid particles may be of a size in the range of from about 50 to 300 μ. A cover 64 is then used to close the housing 30 completing the device.

A third device is depicted in FIGS. 3 and 4. The device 70 is cylindrical, having cylindrical membrane 72 fitted into cylinder 74 which serves as the membrane compartment. An inner tube or sleeve 76 serves for mounting the membrane 72 and to define the silicic acid compartment 80. Silicic acid particles 81 as described previously are then packed into silicic acid compartment 80. First and second screens 82 and 84 respectively are mounted at the bottom and top of compartment 80 to ensure that silicic acid particles do not escape.

The device may be assembled by employing top cap 85 and bottom cap 90 and mounting inner tube 76 on projection 86 which holds the inner tube 76 in place. Included within inner tube 76 is mounting 90 which includes conduit 92, which is in alignment with orifice 94 in innertube 76. Mounting 90 receives and holds first and second screens 82 and 84 in position to prevent the silicic acid particles 81 from entering the membrane compartment 74. The top cap 85 has plasma inlet 96 and plasma outlet 100.

After mounting the inner tube 76 on projection 86, membrane 72 is then fitted onto inner tube 76, followed by mounting of membrane compartment tube 74 which encloses membrane 72. Assemblage of the device is completed by adding the upper silicic acid screens 82 and 84 over the silicic acid, followed by enclosing the device with top cap 85 which includes plasma inlet orifice 96 and plasma outlet 100.

The top of the membrane may be coated with netting 102 which is held in place with a hot melt 104 so as to provide structural stability to the membrane 72.

In using the device, the plasma will enter inlet 96 and flow downwardly through membrane 72. The flow of plasma will be circular around the device, filling the membrane with the plasma. The plasma will reach the bottom of the device and pass through orifice 94 into conduit 92. From conduit 92, the plasma will pass through first and second screens 82 and 84 into the silicic acid particles 81, where anaphylatoxins will be removed. After passing upwardly through the silicic acid particles 81, the plasma will pass through upper screens 82 and 84 through outlet 100.

The membrane may then be easily removed for regeneration or other use by removing the top cap 85 and the membrane compartment 74 and retrieving the membrane 72 by removal from the sleeve or inner tube 76.

Other equipment may be employed with the device, including additional extraction systems. Usually, a pump or an hydraulic device will be employed to move the blood from the patient or other source through the various compartments and conduits. Various alarm and control systems may be employed for detecting rate of flow, flow blockages, air bubbles, clots, or the like. Other components may be additional filters, absorbents, chemical treatments, radiation treatments, and the like. Various electronic equipment may be associated with the device to provide for the automation of various fluid flows, the eluent where the bound material is removed, and the like.

The following examples are for illustration and not by way of limitation.

The device as depicted in FIG. 1 is prepared as follows. A polycarbonate case encloses ten packs of cellulosic membranes, each pack contains ten rectangular sheets of membrane. Each pack is separated from the next by a polypropylene O-ring and a flow-directing U-ring, as well as the polypropylene separation screens. The ten packs are compressed beneath a polycarbonate lid having an access port equal in diameter to the inlet and outlet ports of the polycarbonate case. A 35-60 μ high-density polyethylene filter is applied across the access port to prevent entry of silicic acid particles into the compartment containing the membrane packs. The same filter is placed across the outlet of the silicic acid compartment to prevent the silicic acid from being entrained with the plasma.

The silicic acid has a particle size of 75-250 μ. The polycarbonate lid is then applied.

The receptor is then covalently immobilized to the membrane as described below. By the process of immobilization described below, approximately 400 mg of recombinant protein A (rPA) is covalently attached to the membrane prior to the addition of the silicic acid to the silicic acid compartment. In this manner the subject device contains ten square feet of cellulosic membrane to which is bound approximately 400 mg rPA.

The membrane is prepared by solution casting of cellulose acetate onto a polyester support matrix. The membrane (B10-38) is manufactured by Memtek Corp., Bellenia, Mass. The membrane employes a cellulose material reinforced with a polyester (Dacron) spun-bonded material. The reinforcing web is incorporated in the membrane during membrane formation and is an intergral part of the membrane but does not significantly affect the membrane properties. The membrane has a pore size distribution predominantly in the 1 to 1.5 um range, as represented by the foam point. The membrane is dried, wound on a plastic core, and quality control tested. The membrane is then processed through a series of chemical washes and surface activated by periodate oxidation. The membrane is then thoroughly washed and stabilized with a solution of glycerin and sterile water. After drying, the membrane may be packaged for subsequent use. The ratio of bound rPA to weight of membrane is about 5.5 mg rPA/gram of membrane.

The membrane is further characterized by having a width of about 3.18-3.25 inches, a length of 6.42 to 6.52 inches, a thickness of 175-250 μm, a weight of about 90-125 mg/47 mm disc, a water flux (ml/min/cm$^2$) of about 20-25 inches of Hg, vacuum, and a human IgG binding capacity of about 70 g/cm$^2$. The membranes are substantially non-pyrogenic and non-toxic.

Immobilization of protein is achieved as follows. After the dry weight is recorded and the device purged with carbon dioxide, the device is flushed with 0.2M borate buffer. A 12.6 mg/ml rPA solution in 0.5M borate buffer, pH 9.2, is circulated throughout the device for 11-15 hours at room temperature, followed with flushing with 0.2M borate buffer. The device is then profused with 1.0 mg/ml sodium borohydride in 0.5M borate buffer flushing with 0.2M borate buffer, followed by repeating the borohydride and flushing steps. After flushing the device with 1M sodium chloride at 5° C., the device is flushed with 0.5M glycine-HCl at 35° C. Glycine-HCl (0.5M) is then circulated at 37° C. until the effluent has an optical density of less than about 0.001 at 280 nm. The device is then flushed successively with phosphate buffered saline to a pH of 7.0-7.2, while monitoring to ensure that the optical density remains at the previously defined level, followed by flushing with 0.5% glycerol. The device is then centrifuged at 2,000 rpm for 30 min to facilitate drying, incubated at approximately 40° C. while perfusing with filtered air or nitrogen until the dried weight of each unit is within approximately 10 g of the initial dry weight.

In order to determine whether the covalently bound protein is substantially free of leaching when perfused with plasma or another aqueous medium, the following experiments were carried out. Four ethylene oxide-sterilized prototype devices having polyethylene silicic acid filters, ten square feet of membrane, 400 mg of rPA and 90 g of silicic acid were subjected to the following flush/perfusion protocol. Two 500 ml volumes of 0.9% saline at room temperature were pumped through the device at 200 ml/min and collected separately. A sample was taken of each. Subsequently, two additional 500 ml volumes of 0.9% saline at 37° C. were sequentially pumped through each device at 200 ml/min and collected separately. A sample was taken of each.

An additional 500 ml of 0.9% saline at 37° C. was recirculated continuously through the device at 50 ml/min for 4 h. At the end of this procedure, the saline perfusate was collected separately and a sample taken for assay. All samples were assayed by an rPA specific ELISA assay and by less specific methods (BCA, bi-ocinchoninic acid, and optical density at 210 and 280 nm). The results are indicated in Table 1.

The BCA active material was established to be a contaminant of the assembly used in the flush/perfusion protocol by employing a sham procedure using a tubing and pump assembly identical to the flush/perfusion study, except that the device was not included in the loop. The data showed that negligible (<0.001%) amounts of rPA were detected in eluates from the device during perfusion.

To determine the specificity of binding of the subject device, the following experiments were carried out. Two devices were studied, one with silicic acid and one without silicic acid, where a polyethylene filter was used as described previously. All the devices were sterilized with ethylene oxide. The protocol was as follows.

After priming the device with 1L of a phosphate buffer saline flush, 1.5L normal human plasma was pumped through the device at 50 ml/min in a single pass. Pre- and post-perfusion plasma samples were retained. Earlier data had shown that protein A is saturated by approximately 1-1.5L of normal plasma. Two liter phosphate buffered saline flushes were then followed by two 0.5M acetic acid 2L flushes and samples of the acetic acid washes saved. Both the acetic acid wash samples and the pre/post-plasma were

TABLE 1

LEACHING OF PROTEIN A BY FLUSH/PERFUSION
Four devices having internal polyethylene silicic acid filters.

| Device Item Number | Sample | ELISA (ng/ml) | BCA (mg) | 210 nm (OD units) | 280 nm (OD units) |
|---|---|---|---|---|---|
| 1987 | Flush 1 | <10 | 3.4 | .274 | .031 |
|  | Flush 2 | <10 | 0 | .131 | .014 |
|  | Flush 3 | 15 | 0 | .090 | .012 |

TABLE 1-continued

LEACHING OF PROTEIN A BY FLUSH/PERFUSION
Four devices having internal polyethylene silicic acid filters.

| Device Item Number | Sample | ELISA (ng/ml) | BCA (mg) | 210 nm (OD units) | 280 nm (OD units) |
|---|---|---|---|---|---|
| | Flush 4 | 10 | 0 | .056 | .009 |
| | Perfusion | 96 | 1.55 | .242 | .023 |
| 1990 | Flush 1 | 10 | 0 | .442 | .036 |
| | Flush 2 | <80 | 0 | .141 | .020 |
| | Flush 3 | 83 | 0 | .084 | .017 |
| | Flush 4 | 11 | 0 | .058 | .013 |
| | Perfusion | 109 | 0 | .144 | .023 |
| 2000 | Flush 1 | 12 | 0 | .178 | .089 |
| | Flush 2 | <80 | 0 | .098 | .016 |
| | Flush 3 | <80 | 0 | .060 | .009 |
| | Flush 4 | 12 | 0 | .034 | .006 |
| | Perfusion | 80 | 0 | .116 | .01 |
| 2004 | Flush 1 | 11 | 0 | .186 | .014 |
| | Flush 2 | <80 | 0 | .116 | .004 |
| | Flush 3 | 115 | 0 | .055 | .005 |
| | Flush 4 | 13 | 0 | .039 | .001 |
| | Perfusion | 80 | 1.35 | .107 | .007 | analyzed by a Bradford assay kit (Bio-Rad 500-001). The difference between pre- and post- samples minus that contained in residual plasma represents total IgG binding, while the specifically bound IgG is the result obtained from the acetic acid washes. This is also the recoverable IgG.

Table 2 indicates the results.

TABLE 2

IgG BINDING BY PROTOTYPE DEVICES

| Device Item Number | Specificity Binding (grams) | Total IgG Binding (grams) |
|---|---|---|
| A. IgG binding by 15 ft² device having 750μ rPA* but no silicic acid compartments | | |
| 1767 | 0.874 | 2.64 |
| 1768 | 0.910 | 3.51 |
| 1747 | 1.015 | 1.49 |
| 1753 | 0.80 | 7.50 |
| 1734 | 1.246 | 5.05 |
| 1737 | 1.326 | 3.96 |
| 1718 | 1.540 | 3.00 |
| mean | 1.10 | 3.88 |
| B. IgG binding by assembled device having polyethylene filters (10 ft², 400 mg rPA, 90 gm silicic acid). | | |
| 1987 | 1.037 | 2.685 |
| 1990 | 0.959 | 2.550 |
| 2000 | 0.805 | 3.735 |
| 2004 | 0.912 | 2.390 |
| mean | 0.928 | 2.84 |

*rPA = recombinant Protein A.

The above results demonstrate that the subject device, with or without the silicic acid compartment, effectively and consistently binds IgG from human plasma. Based on the above data, a mean value of approximately 3.0 g total IgG is bound from 1500 ml of processed plasma.

In another study, the preference for immune complex over uncomplexed immunoglobulin was established by monitoring the complex and monomer before and after passage through the device. As the results show, the bound rPA finally became saturated with immune-complex which displaced the initially bound monomer.

To further evaluate the effectiveness of the device, the acetic acid washes were concentrated, the concentrated eluate desalted and applied to an IEP plate and developed with antibodies against IgG, IgM and whole serum proteins. The results showed that only IgG and IgM were present in the eluate with no other plasma proteins present. Thus, only those ligands which specifically bind to the rPA receptor were bound and removed from the plasma through the device.

Another area of concern is platelets. For the most part, platelets will not be efficiently removed by the usual technique employed for removal of cells from blood, namely centrifugation. Therefore, the device was tested to determine whether platelets would clog the device and what effect the device would have on the viability and state of the platelets.

During four routine plasma exchange procedures on the IBM Model 2997 Blood Cell Separator, the device was connected on-line between the plasma pump and filtrate collection bag. Three way stop cocks were spliced in line just before and just after the device to permit pre-device and post-device sampling. Plasma samples, as paired pre/post-samples, were collected at 5, 25 and 45 min into the exchange procedure. These times correspond with approximate exchange volumes of 0.5, 1.0 and 1.5L from a total of 3L procedures. To determine the platelet-device interaction, the following measurements were made on paired samples: platelet count; beta-thromboglobulin (BTG) level; and intra-platelet serotonin level. After each procedure, the device were grossly examined for evidence of platelet "clumping" and aggregation.

Tables 3 through 6 indicate the results using a 15 ft² device with approximately 500 mg rPA bound and without a silicic acid compartment.

These results show that in a fully functional device ($I_gG$ was bound by the membrane) although some platelets are bound in the device, the fluid path is not affected (plasma continues to flow freely), the platelets bound in the device are not activated (minimal changes in beta.thromboglobulin levels) and the platelets passing through the device are fully functional (no change in intra-platelet serotonin levels). The device is thus neutral with respect to platelet function.

TABLE 3

PLATELET COUNTS IN PLASMA PRE/POST DEVICE AT VARIOUS TIME INTERVALS

| Device Item Number | Patient Baseline Count | Time Into Exchange | Pre Device | Post Device | % Change |
|---|---|---|---|---|---|
| 1508 | 302,000 | 5 min. | 61,000 | 30,000 | −51% |
| | | 25 min. | 85,000 | 51,000 | −40% |
| | | 45 min. | 59,000 | 40,000 | −32% |
| 1509 | 418,000 | 5 min. | 96,000 | 30,000 | −69% |
| | | 25 min. | 59,000 | 35,000 | −41% |
| | | 45 min. | 30,000 | 29,000 | −3% |
| 1510 | 458,000 | 5 min. | 695,000 | 457,000 | −34% |
| | | 25 min. | 94,000 | 61,000 | −35% |
| | | 45 min. | 344,000 | 295,000 | −14% |
| 1511 | 217,000 | 5 min. | 52,000 | 76,000 | +46% |
| | | 25 min. | 46,000 | 27,000 | −41% |
| | | 45 min. | 37,000 | 20,000 | −46% |

TABLE 4

**BETA THROMBOGLOBULIN* MEASUREMENT IN PLASMA ENTERING AND EXITING THE DEVICE**

| Device Item Number | Time Into Exchange | BTG (ng/ml) Pre-Device | BTG (ng/ml) Post-Device |
|---|---|---|---|
| 1508 | 5 min. | 36 | ND** |
| | 25 min. | 32 | 123 |
| | 45 min. | 32 | 170 |
| 1509 | 5 min. | ND | ND |
| | 25 min. | 41 | 45 |
| | 45 min. | 46 | 64 |

TABLE 4-continued

BETA THROMBOGLOBULIN* MEASUREMENT IN
PLASMA ENTERING AND EXITING THE DEVICE

| Device Item Number | Time Into Exchange | BTG (ng/ml) Pre-Device | BTG (ng/ml) Post-Device |
|---|---|---|---|
| 1510 | 5 min. | ND | ND |
|  | 25 min. | 96 | 100 |
|  | 45 min. | 88 | 210 |
| 1511 | 5 min. | 18 | 26 |
|  | 25 min. | 28 | 64 |
|  | 45 min. | 32 | 108 |

*Normal plasma range for BTG is 24-28 ng/ml
**ND = not determined. Certain samples were omitted from test as only enough reagent for 19 evaluations was available.

TABLE 5

INTRAPLATELET SEROTONIN LEVELS IN PLATELETS
FROM PLASMA PRE- AND POST-DEVICE

| Device Item Number | Time Into Exchange | Intraplatelet Serotonin Levels (ng/10⁹ platelets)* Pre-Device | Intraplatelet Serotonin Levels (ng/10⁹ platelets)* Post-Device |
|---|---|---|---|
| 1508 | 5 min. | 250 | 250 |
|  | 25 min. | 235 | 235 |
|  | 45 min. | 230 | 225 |
| 1509 | 5 min. | 140 | 140 |
|  | 25 min. | 145 | 140 |
|  | 45 min. | 290 | 290 |
| 1510 | 5 min. | 110 | 90 |
|  | 25 min. | 80 | 80 |
|  | 45 min. | 55 | 55 |
| 1511 | 5 min. | 211 | 86 |
|  | 25 min. | 270 | 270 |
|  | 45 min. | 230 | 230 |

*Normal range is 300-980 ng/10⁹ platelets

TABLE 6

TOTAL PROTEIN FROM PLASMA
ENTERING AND EXITING THE DEVICE

| Device Item Number | Time Into Exchange | Pre-Device | Post-Device |
|---|---|---|---|
|  |  | Total Protein (gm/100 ml) | |
| 1508 | 5 min. | 4.8 | 2.5 |
|  | 25 min. | 4.2 | 4.0 |
|  | 45 min. | 4.2 | 3.9 |
| 1509 | 5 min. | 5.5 | 4.2 |
|  | 25 min. | 5.8 | 5.5 |
|  | 45 min. | 5.8 | 5.8 |
| 1510 | 5 min. | 4.3 | 3.0 |
|  | 25 min. | 4.8 | 4.6 |
|  | 45 min. | 5.2 | 4.8 |
| 1511 | 5 min. | 5.2 | 3.2 |
|  | 25 min. | 4.5 | 4.2 |
|  | 45 min. | 4.0 | 4.0 |
|  |  | IgG Measurement (gm/L)** | |
| 1508 | 25 min. | 5.55 | 4.18 |

*Drop in this sample mainly due to dilution.
**Normal range is 8-18 gm/L.

The next study was to demonstrate the device could be used to remove specific proteins from plasma for example tumor necrosis factor (TNF) which is involved in septic shock.

Outdated normal human plasma was employed. The plasma was divided into 2×1L volumes and 17 µg of ³⁵S-TNF was added to each liter to give a total 5.1×10⁶ cpm/L. One ml of each preparation was counted in a 5 ml Optofluor to obtain a pre-perfusion radioactivity measurement. The TNF had been labeled with ³⁵S-methionine in accordance with conventional techniques. Counting of input and output plasma samples by liquid scintillation provided direct measurements of TNF in the plasma The device had a 4 ft² path with monoclonal α-TNF bound as described for rPA. There was no silicic acid compartment. The amount of TNF bound by the device was derived by subtracting the amount remaining in the plasma after perfusion (output plasma) from the amount of TNF in the input plasma. The fraction of immunoactive radio-labeled TNF was determined using a solid-phase radioimmunoassay in which excess antibody was immobilized. Briefly, 10, 25, 50, 100, 125, 150 and 200 µl of a 100 µg/ml stock of an anti-TNF monoclonal antibody in 0.5M carbonate buffer (pH 9.0) were added to Removawells (Dynatech Immulon I) and incubated overnight at 4° C. The wells were blocked with 200 µl 5% BSA in the carbonate buffer for 2 h at room temperature. The wells were washed a minimum of 6× with PBS and 5 or 50 µg of ³⁵S-TNF in 200 µl of PBS was added to each well and the wells incubated at room temperature for 1.5 h. At the end of the incubation, the solution in each well was transferred as completely as possible to a scintillation vial and counted. The individual wells were also counted. The percent CPM bound (CPMs on wells/(CPMs on wells 30 CPMs in solution) ×100% was plotted against the amount of adsorbed anti-TNF monoclonal antibodies/well. The percent immunoactive ³⁵S-TNF was then taken as the plateau value from the above plot. These results provided for the binding activity of the ³⁵S-TNF.

The plasma containing ³⁵S-TNF was passed through the preiously described device (a device having bound human IgG was employed as a control) at a flow rate of 50 ml/min for 3 h at room temperature. At the end of 1, 2, and 3 h of perfusion, 1 ml aliquots were withdrawn from the plasma reservoir and counted. Each device was perfused with 5×500 ml saline for 10 min at room temperature at a flow rate of 150 ml/min. One ml aliquots of each rinse were counted. The devices were then eluted with up to 5×100 ml 4M magnesium chloride. After each elution, 1 ml aliquots were withdrawn and counted. Tables 7 and 8 indicate the results.

TABLE 7

DEPLETION OF TNF FROM PLASMA BY DEVICE

| Sample | Anti-TNF Device TNF Removed¹ (µg) | Anti-TNF Device Immunoreactive ³⁵S-TNF Removed¹,² (%) | Control Device TNF Removed¹ (µg) | Control Device Immunoreactive ³⁵S-TNF Removed¹,² (%) |
|---|---|---|---|---|
| 1 hr | 7.5 | 68.8 | 1.1 | 10.1 |
| 2 hr | 7.8 | 71.6 | 0.9 | 8.3 |
| 3 hr | 8.1 | 74.3 | 0.3 | 2.8 |

¹Cumulative values
² (µg TNF removed)/10.5 µg × 100%

TABLE 8

RECOVERY OF BOUND TNF
FROM DEVICE BY 4 M MgCl₂ ELUTION

| 4M MgCl₂ Elution | Anti-TNF Device TNF (µg) | Anti-TNF Device Recovery¹ (%) | Control Device TNF (µg) | Control Device Recovery¹ (%) |
|---|---|---|---|---|
| 1st Eluate | 2.0 | 24.7 | 0.2 | 40.0 |
| 2nd Eluate | 2.3 | 28.4 | 0.1 | 20.0 |
| 3rd Eluate | 1.5 | 18.5 | 0.0 | 0.0 |
| 4th Eluate | 0.6 | 7.4 | — | — |
| 5th Eluate | 0.2 | 2.5 | — | — |

TABLE 8-continued

| | RECOVERY OF BOUND TNF FROM DEVICE BY 4 M MgCl₂ ELUTION | | | |
|---|---|---|---|---|
| | Anti-TNF Device | | Control Device | |
| 4M MgCl₂ Elution | TNF (μg) | Recovery[1] (%) | TNF (μg) | Recovery[1] (%) |
| Total | 6.6 | 81.5 | 0.3 | 60.0 |

[1] Values calculated from
$$\frac{(\mu g \text{ in eluate})}{(\text{total } \mu g \text{ TNF removed after 3 h})} \times 100\%$$

Based on binding activity, it was found that the immunobinding activity of ³⁵S-TNF was about 64.1%. This immunoreactivity level was then factored into the subsequent calculations from results of plasma perfusion and magnesium chloride elution. The above tables show that 74.3% TNF was removed by the anti-TNF device from 1L plasma containing 1 nm TNF in a 3 h perfusion. By comparison, the control device removed only 2.8% TNF. In addition, the results show that 81.5% of bound TNF was recovered from the device.

In the next study, the removal of anti-DNA antibody from the sera of patients with systemic Lupus Erythematosus is investigated. The adsorbent employs polystyrene beads (500 μ) which are prepared as described in application Ser. No. 051,917, filed May 19, 1987. Calf thymus DNA (10 mg/ml) is sonicated using a fine-tipped probe over 1 h, using a pulsed delivery. The sheared DNA has an average size of about 500-1500 bp. The sheared DNA is then extracted 2× with phenol-chloroform and precipitated with ethanol. The sheared DNA is then resuspended to 10 mg/ml and stored in 5 ml aliquots at −20° C. until used. Polystyrene beads (Precision Plastic Ball beads) in cold 0.05M sulfuric acid (5 ml) are added to a cold 50 ml polypropylene centrifuge tube, the supernatant removed and 45 ml of cold 2% sodium nitrite in 1M HCl added. After mixing on a platform rocker for 30 min at 4° C., the beads are collected on a cold 15 ml sintered glass filter using vacuum suction, washed with 100 ml cold 0.5M H₂SO₄, followed by 200 ml cold water. The drained beads are then added to a cold 50 ml polypropylene centrifuge tube, followed by the addition of 10 ml of 5 mg/ml ³²P-DNA in cold 0.025M borate buffer, pH 9.2 and the mixture incubated overnight at 4° C. on a platform rocker. Supernatant is transferred to a 10 ml polypropylene tube, the labeled beads washed 15× with 50 ml water, 2× with 2M sodium chloride and 15× with water. A 0.125 ml aliquot of beads is counted to provide 40,000 cpm in 5 ml packed volume of the DNA beads.

By replacing the membranes with the subject beads and perfusing the beads in the manner described previously, with plasma samples from patients having anti-DNA, the anti-DNA antibody will bind to the DNA, to provide a plasma effluent substantially free of autoantibody.

It is evident from the above results, that the subject devices have a wide variety of applications, in diagnosis and therapy, and in providing for a source of modified plasma. Despite the harsh conditions employed for fluid flow, high efficiencies are obtained in the removal of specific components, while at the same time little if any loss is observed of the materials bound to the supports. In addition, high recoveries are achieved from materials which are bound, substantially free of other components of the streams passed through the device, as well as free of the binding components bound to the support in the device.

The subject device can be used for therapeutic purposes, in removing materials adverse to a host, such as immune complexes, tumor necrosis factor, and the like. In addition, the device may be used for diagnosis, by eluting and identifying the particular materials which have become bound. In the case of immune complexes, the complexes may be isolated and the antigen assayed to determine the source which provoked the immune response. Thus, the subject devices have a multiplicity of utilities and structures and provide a safe and effective way to modify plasma and obtain information from the plasma which may be used in diagnosis and therapy.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A device for modifying plasma by removing or remodeling at least one plasma component, which plasma component is a member of a specific binding pair, said device having a predetermined volume rating, said device comprising:
   - a container of a biocompatible material having an entry and an exit port and an extended flow path between said ports;
   - a high surface area biocompatible cellulosic porous solid support comprising a member of said specific binding pair substantially uniformly and irreversibly bonded to said support in an amount sufficient to bind the reciprocal member of said specific binding pair at the volume rating of said device, wherein said flow path directs said plasma through said porous support;
   - said porous support comprising membrane sheets in stacks of at least two sheets, there being at least two stacks;
   - separating said stacks are alternating U-rings in alternate directions to alternately direct the flow path in opposite directions.

2. A device according to claim 1, wherein said cellulosic support is a cellulose acetate coating on a polyester membrane carrier.

3. A device according to claim 2, wherein said specific binding member is a protein bonded to said support by reductive amination.

4. A device according to claim 3, wherein said protein specifically binds to immunoglobulin.

5. A device according to claim 4, wherein said protein is recombinant protein A.

6. A device according to claim 3, wherein said protein is a membrane surface receptor.

7. A device according to claim 6, wherein said membrane surface receptor is acetylcholine receptor.

8. A device according to claim 2, comprising in combination in fluid receiving relationship with said exit port a silicic acid anaphylatoxin removing compartment.

* * * * *